United States Patent [19]

Kluender et al.

[11] 4,127,612
[45] Nov. 28, 1978

[54] 19-HYDROXY PGE$_1$ CARBINOL ANALOGUES

[75] Inventors: Harold C. Kluender; Warren D. Woessner, both of Madison, Wis.

[73] Assignee: Miles Laboratories, Inc., Elkhart, Ind.

[21] Appl. No.: 887,666

[22] Filed: Mar. 17, 1978

[51] Int. Cl.$^2$ ............................................. C07C 177/00
[52] U.S. Cl. ............................ 260/586 R; 568/598; 568/845; 260/438.1
[58] Field of Search ........................................ 210/586 R

[56] References Cited
U.S. PATENT DOCUMENTS
4,054,595  10/1977  Marx et al. ..................... 260/438.1

OTHER PUBLICATIONS
FEBS Letters, 57, 22 (1975).
Science, 187, 1093 (1975).
Sih, Prostaglandins, 13, 830 (1977).

Primary Examiner—Gerald A. Schwartz
Attorney, Agent, or Firm—James D. McNeil

[57] ABSTRACT

19-Hydroxy carbinol analogues of PGE$_1$ having the structure

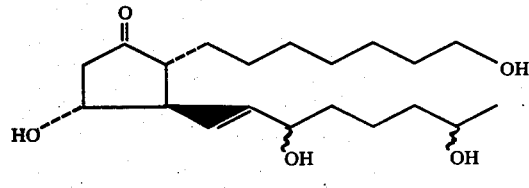

are disclosed as bronchodilators.

Methods of preparing the analogues are also disclosed.

3 Claims, No Drawings

19-HYDROXY PGE₁ CARBINOL ANALOGUES

BACKGROUND OF THE INVENTION

1. Field of the Invention

The compounds of this invention are analogues of natural prostaglandins.

Natural prostaglandins are alicyclic compounds related to prostanoic acid, the structure of which is:

[Structure I: prostanoic acid numbered 1-20]

By convention, the carbon atoms of I are numbered sequentially from the carboxylic carbon atom. An important stereochemical feature of I is the trans-orientation of the sidechains $C_1-C_7$ and $C_{13}-C_{20}$, an orientation common to all natural prostaglandins. In I, as elsewhere in this specification, solid lines (—) provide a reference plane (such as the cyclopentyl ring or the bonds among atoms $C_1-C_7$ and $C_{13}-C_{20}$); a dashed line (- - - -) indicates projection of a covalent bond below such reference plane (alpha-configuration); while a wedged line (◂━) represents direction above such plane (beta-configuration). In some structures, however, a swung dash or serpentine line (∼) denotes orientation of a covalent bond either abobe or below a plane of reference (indicated by the Greek letter xi in the nomenclature of such structures).

Natural prostaglandins have the general structure,

[Structure II]

in which: L and M may be ethylene or cis-vinylene radicals; and the cyclopentyl ring CP may be:

[A-class];
[B-class];
[C-class];
[D-class];
[E-class];
[Fα-class];

or

Formula II and all representations of the cyclopentyl moiety depict the nat-isomer, i.e., the $C_7-C_8$ bond in the alpha-configuration and the $C_{12}-C_{13}$ bond in the beta-configuration. In the ent-isomer (which does not occur in nature), the direction of the bonds at $C_7-C_8$ and $C_{12}-C_{13}$ is reversed.

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}-C_{11}$ ($\Delta^{10,11}$); those of the B-class (PGB) have an oxo group at $C_9$ and a double bond at $C_8-C_{12}$ ($\Delta^{8,12}$); compounds of the C-class (PGC) contain an oxo group at $C_9$ and a double bond at $C_{11}-C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the $F_\alpha$-class (PGF$_\alpha$) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5-C_6$, $C_{13}-C_{14}$, or $C_{17}-C_{18}$. The presence of a trans-unsaturated bond only at $C_{13}-C_{14}$ is indicated by the subscript numeral 1; thus, for example, PGE₁ (or prostaglandin E₁) denotes a prostaglandin of the E-type (oxo-group at $C_9$ and an alpha-hydroxyl at $C_{11}$) with a trans-double bond at $C_{13}-C_{14}$. The presence of both a trans-double bond at $C_{13}-C_{14}$ and a cis-double bond at $C_5-C_6$ is denoted by the subscript numeral 2; for example, PGE₂. Lastly, a trans-double bond at $C_{13}-C_{14}$, a cis-double bond at $C_5-C_6$ and a cis-double bond at $C_{17}-C_{18}$ is indicated by the subscript numeral 3; for example, PGE₃. The above notations apply to prostaglandins of the A, B, C, D, and F series as well; however, in the last, the alpha-orientation of the hydroxyl group at $C_9$ is indicated by the subscript Greek letter α after the numerical subscript.

Nomenclature of prostaglandins and their analogues deserves note insofar as there are three current systems followed in the scientific and patent literature. One system for convenience referred to as the Nelson system, uses the trivial names of prostaglandins and designates analogues by modifications of the trivial names (see—*J. Med. Chem.*, 17; 911 [1974]). Another system follows the rules of the International Union of Pure and Applied Chemistry (IUPAC) and refers to prostaglandins and their analogues as derivatives of heptanoic acid. A third system employs a convention of Chemical Abstracts ("CA") that designates prostaglandins and derivatives thereof as derivatives of prostanoic acid. An example of each system is provided below for the following structure:

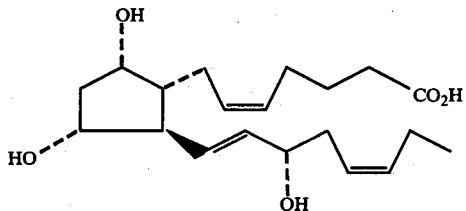

III.

In the Nelson system, III is designated prostaglandin $F_{3\alpha}$ or $PGF_{3\alpha}$ (shortened form); in the IUPAC system, 7-[3R,5S-dihydroxy-2R-(3S-hydroxy-1E,5Z-octadienyl)-cyclopent-1R-yl]-5Z-heptenoic acid; in the CA system, (5Z,9α,11α,13E,15S,17Z)-9,11,15-trihydroxyprosta-5,13,17-trien-1-oic acid.

It is important to note that in all natural prostaglandins there is a hydroxyl group at $C_{15}$ oriented below the plane in which $C_{15}$ is located. In the Cahn-Ingold-Prelog system of defining stereochemistry, that $C_{15}$ hydroxyl group is in the S-configuration. Inversion of the orientation of the $C_{15}$ hydroxyl group such that the group projects above the plane in which the $C_{15}$ atom is located represents the R-configuration. The Cahn-Ingold-Prelog system is used to define stereochemistry of any asymmetric center outside of the carbocyclic ring in all three systems of nomenclature described above. In some literature, however, α,β designations are used for such centers.

Isomerism of a double bond is designated in all three systems by use of conventional prefixes cis- to trans-, or their respective equivalents, Z or E (as suggested in *J. Am. Chem. Soc.*, 59: 509 [1968]).

For details of other conventions utilized in nomenclature of prostaglandins, see: Nelson, N. A., "Prostaglandin Nomenclature", *J. Med. Chem.*, 17: 911 (1974).

Recent research indicates that prostaglandins appear ubiquitously in animal tissues and elicit biochemical and physiological effects in a variety of mammalian systems.

In the endocrine system, for example, experimental evidence indicates prostaglandins influence the hormone synthesis or release of hormones in the secretory glands. In rats, $PGE_1$ and $PGE_2$ increase the release of the growth hormone while $PGA_1$ increases its synthesis. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate stereoidogenesis in the adrenal glands.

In the mammalian male reproductive system, $PGE_1$ contracts the smooth muscle of the vas deferens In the female reproductive system, PGE and $PGF_\alpha$ compounds contract uterine smooth muscle. In general, PGE, PGB and PGA compounds relax in vitro human uterine muscle strips, while those of the $PGF_\alpha$ class contract such isolated preparations. PGE compounds, in general, promote fertility in the female reproductive system while $PGF_{2\alpha}$ has contragestational effects. $PGF_{2\alpha}$ also appears to be involved in the mechanism of menstruation. In general, $PGE_2$ produces potent oxytocic effects in inducing labor, while $PGF_{2\alpha}$ induces spontaneous abortions in early pregnancy.

$PGF_\alpha$ and PGE compounds have been isolated from a variety of nervous tissues. $PGE_1$ retards whereas $PGF_{2\alpha}$ facilitates transmission along motor pathways in the central nervous system. $PGE_1$ and $PGE_2$ reportedly inhibit transmitter release from adrenergic nerve endings in the guinea pig.

Prostaglandins stimulate contraction of gastrointestinal smooth muscle in vivo and in vitro. In dogs, $PGA_1$, $PGE_1$, and $PGE_2$ inhibit gastric secretion. $PGA_1$ exhibits similar activity in man. Natural prostaglandins and some of their analogues also protect gastric mucosa from ulceration induced by nonsteroidal antiinflammatory agents.

In most mammalian respiratory tracts, PGE and PGF compounds affect in vitro preparations of tracheal smooth muscle. Specifically, $PGE_1$ and $PGE_2$ relax while $PGF_{2\alpha}$ contracts such smooth muscle. The human lung normally contains PGE and PGF compounds; consequently, some cases of bronchial asthma may involve an imbalance in the production of metabolism of those compounds.

Prostaglandins are involved in certain hematic mechanisms in mammals. $PGE_1$, for example, inhibits aggregation of blood platelets in vitro.

In a variety of mammalian cardiovascular systems, compounds of the PGE and PGA classes are vasodilators whereas those of the $PGF_\alpha$ class are vasoconstrictors, by virtue of their action on vascular smooth muscle.

Prostaglandins naturally appear in the kidney and reverse experimental and clinical renoprival hypertension.

The prostaglandins and their analogues have broad clinical implications. In obstetrics and gynecology, they may find use in fertility control, treatment of menstrual disorders, the induction of labor, and the correction of hormone disorders. In gastroenterology, they may help treat or prevent peptic ulcers and various disorders involving motility, secretion, and absorption in the gastrointestinal tract. They may, in the respiratory area, prove beneficial in the therapy of bronchial asthma and other diseases involving bronchoconstriction. In hematology, they may display utility as anti-clotting agents in diseases such as venous thrombosis, thrombotic coronary occlusion and other diseases involving thrombi. For circulatory diseases, they have therapeutic utility in hypertension, peripheral vasopathies and cardiac disorders.

The following references include a more complete review of the chemical, physiological and pharmacological aspects of the prostaglandins: *The Prostaglandins*, Vol. I., P. Ramwell, Ed., New York, Plenum Press, 1973; *Ann. N.Y. Acad. Sci.*, 180: 1–568 (1971); Higgins and Braunwald, *J. Am. Med. Assn.*, 53: 92–112 (1972); Osterling, Marozowich, and Roseman, *J. Phar. Sci.*, 61: 1861–1895 (1972); and Nakano, *Resident and Staff Phys.*, 19: 92, 94–99, and 102–106 (1973).

DESCRIPTION OF THE PRIOR ART

The compounds 19R-hydroxy $PGE_1$; $-PGE_2$; $-PGF_{2\alpha}$ and $PGF_{1\alpha}$ esters are naturally occurring and are the major prostaglandin components of human semen [*FEBS Letters*, 57, 22 (1975); *Science*, 187, 1093 (1975)]. A method for preparation of 19R-hydroxy- PGE₁ methyl ester and PGE₂ methyl ester is disclosed by J. C. Sih in *Prostaglandins*, 13, 830 (1977).

None of the above prior art discloses or suggests the carbinol analogue of 19-hydroxy-PGE₁.

SUMMARY OF THE INVENTION

The instant invention is directed to:

(a) Prostaglandin analogues having utility as bronchodilators, having the structural formula:

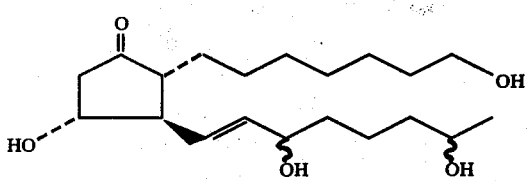
IV.

Included in this genus are:
1,11α,15R,19RS-tetrahydroxyprost-13E-en-9-one; and
1,11α,15S,19RS-tetrahydroxyprost-13E-en-9-one;

(b) methods of synthesizing a prostaglandin analogue having the structural formula IV by reacting an organolithiocuprate having the structural formula V:

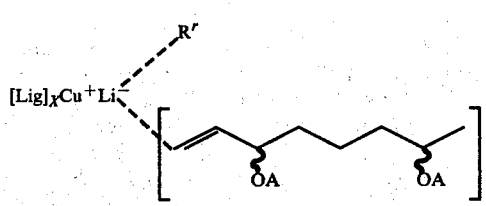
V;

wherein:

Lig represents a solubilizing ligand. Generally Lig is a tri-(di-alkylamino)phosphine of 6–12 carbon atoms, trialkylphosphine having 3–12 carbon atoms, diarylphosphine, dialkylsulfide having 4–8 carbon atoms, arylsulfide or di-(trialkylsilyl)amino having 6–12 carbon atoms. Specifically Lig can be a tri-(dimethyl-amino)phosphine, tri-(n-butyl)phosphine, diphenylphosphine, diisopropylsulfide, dibutylsulfide, phenylsulfide, or di(trimethylsilyl-)amino group, and R' is iodide, thiophenylate, alkyn-1-yl having 3 to 8 carbon atoms or

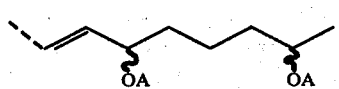

with a substituted 2-cyclopenten-1-one having the structural formula VI:

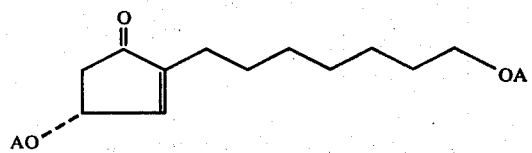
VI;

to form a compound having the structural formula IVa:

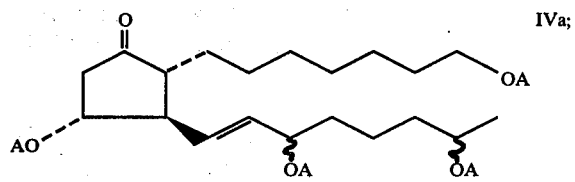
IVa;

wherein A is an acid-labile hydroxyl-protecting group selected from the group consisting of tetrahydropyran-2-yl, trialkylsilyl, triarylsilyl, alkoxyalkyl having from 2 to 6 carbon atoms and triarylmethyl, and acidifying and hydrolyzing the mixture to yield a prostaglandin having the structural formula IV.

(c) 1-iodo-3RS,7RS-dihydroxy-1E-octene, having the structural formula VII,

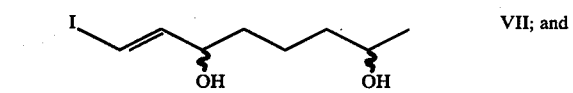
VII; and (d) 1-iodo-3RS,7RS-bis(1-ethoxyethoxy)-1E-octene, having the structural formula VIII:

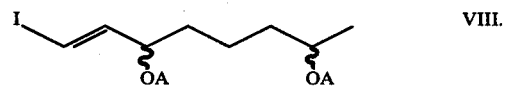
VIII.

DETAILED DESCRIPTION OF THE INVENTION

The prostaglandin analogues of the present invention are prepared via the 1,4-conjugate addition of a substituted 2-cyclopenten-1-one and an organolithiocuprate as reported by Sih, et al., [*J. Amer. Chem. Soc.*, 97: 857, 865 (1975) and references cited therein]. The reaction proceeds in a variety of inert solvent systems of which ether, tetrahydrofuran, hexane, pentane or toluene are representative. The inert atmosphere can be provided by the use of argon or nitrogen. The prostaglandin analogues are prepared according to the reaction sequence depicted in Table A, described hereinafter.

The reaction of a hydroxyl-protected substituted 2-cyclopenten-1-one, for example, 4R(1-ethoxyethoxy)-2-[7-(1-ethoxyethoxy)heptyl]cyclopenten-1-one, having the formula VI:

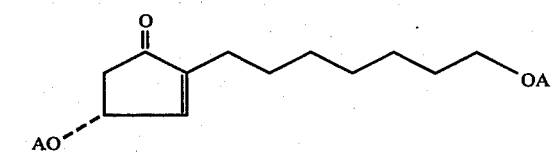

with the organolithiocuprate having the formula V:

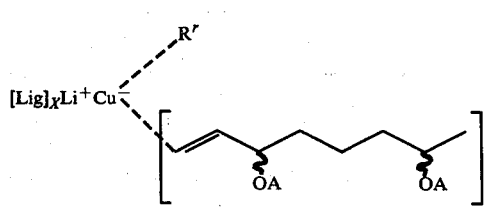

in an inert solvent, under an inert atmosphere at a temperature of from −80° to +10° C. for about 0.25 to 3 hours provides the hydroxyl-protected compound IVa.

droxyprost-13E-en-9-one, both of which are racemic at the $C_{19}$ position.

NMR spectra of the 15R and 15S isomers of 1,11α-15RS,19RS-tetrahydroxyprost-13E-en-9-one were de-

TABLE A

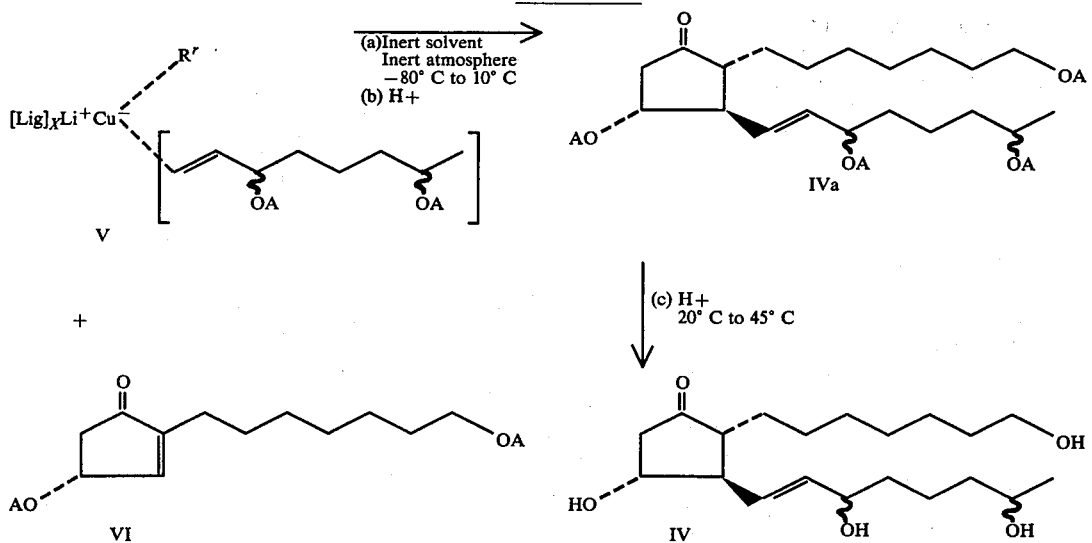

Hydrolysis of the above compound replaces the hydroxyl-protecting group A with hydrogen and provides a mixture of the 15R and 15S isomers, 1,11α,15RS,19RS-tetrahydroxyprost-13E-en-9-one.

Chemical hydrolysis can be accomplished by treatment with a weekly-acidic water mixture, e.g., acetic acid-water (65:35 VV) with 10 percent tetrahydrofuran, at a temperature of about 20° to 45° C. for about 0.5 to 48 hours.

Present in the mixture are:
1,11α,15RS,19RS-tetrahydroxyprost-13E-en-9-one;
1,11α,15R,19RS-tetrahydroxyprost-13E-en-9-one;
1,11α,15S,19RS-tetrahydroxyprost-13E-en-9-one;
1,11α,15R,19S-tetrahydroxyprost-13E-en-9-one;
1,11α,15R,19R-tetrahydroxyprost-13E-en-9-one;
1,11α,15S,19R-tetrahydroxyprost-13E-en-9-one;
1,11α,15S,19S-tetrahydroxyprost-13E-en-9-one.

The compounds of this invention can be isolated from the reaction mixture and purified by well-known organic chemistry procedures. For example, the above prostaglandin analogues can be isolated by dilution of the reaction mixture with water, extraction with a water-immiscible solvent such as benzene, cycohexane, ether, ethyl acetate, methylene chloride, toluene or the like; chromatography; distillation or a combination of these procedures. Purification of these compounds can be accomplished by methods which are well-known in the art for the purification of prostaglandins, lipids, fatty acids, and fatty esters. Such methods as reverse phase partition chromatography; countercurrent distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the process of this invention.

The reaction mixture was treated as described hereinafter to yield two mixtures; 1,11α,15R,19RS-tetrahydroxyprost-13E-en-9-one, and 1,11α,15S,19RS-tetrahytermined in $CDCl_3$ and infrared (ir) spectra in $CHCl_3$ unless otherwise noted. Analytical thin layer chromatography was performed on 0.1 mm Silica Gel 60 F254 plates and preparative thin-layer chromatography was performed using 2.0 mm Silica Gel 60 F254 plates. Spots were visualized under uv light and/or by ceric sulfate spray reagent [See K. Schreiber, et. al., *J. Chromatography*, 12, 63 (1962)]. Column chromatographic separations were perfomed on silica gel using a hexaneethyl acetate or ethanol-ethyl acetate.

A. Preparation of Substituted 2-Cyclopenten-1-one

The substituted 2-cyclopenten-1-one, 4R(1-ethoxyethoxy)-2-[7-ethoxyethoxy)heptyl]-2-cyclopenten-1-one, was prepared as described in *Tetrahedron Letters*, 2063 (1977).

B. Brief Description of the Preparation of Iodovinyl diol and Organolithiocuprate The preparation of the organolithiocuprate used in the present invention is depicted in Table B below and described in detail following Table B.

The organolithiocuprate utilized in the reaction is prepared in solution prior to reaction with the substituted 2-cyclopenten-1-one, and is represented by formula V:

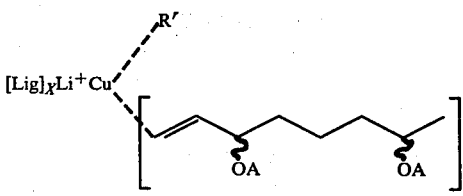

The organolithiocuprate is prepared from the substituted iodovinyl diol of structure XIII. In turn, the substituted iodovinyl diol is prepared from the appropriate ketoacid IX through a chloro intermediate of structure XI. The hydroxyl function of the substituted iodovinyl diol is protected with an acid-labile hydroxy-protecting group.

The hydroxy-protected substituted iodovinyl diol of structure XIV is then lithiated with t-butyllithium and reacted with a solubilized Lig complex of a copper(I) compound such as (hexamethylphosphorus triamide)$_2$-copper(I)pentyne to yield the desired organolithiocuprate.

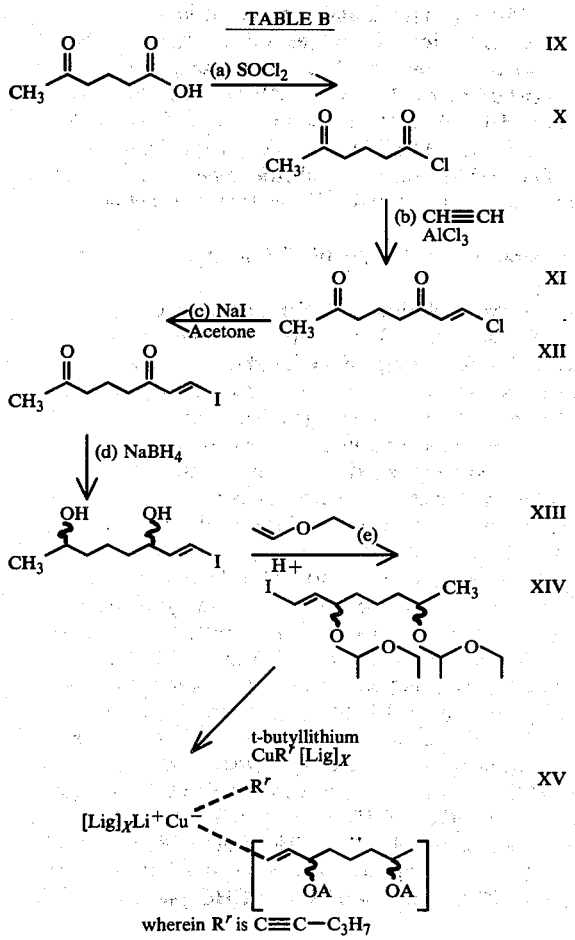

Preparation of Substituted Iodovinyldiol and Organolithiocuprate

As shown in Table B, 5-ketohexanoic acid IX was reacted with thionyl chloride. The reaction mixture yielded 5-ketohexanoylchloride X which was recovered after distillation. The 5-ketohexanoyl chloride X intermediate was reacted with acetylene and aluminum chloride and converted into the chloro-diketone compound XI. The diketone compound was converted into the corresponding iodovinyl diol XIII by adding to the reaction mixture sodium iodide in a solvent such as acetone, and reducing the intermediate compound XII to the diol by adding sodium borohydride.

The hydroxyl-group of the iodovinyl diol XIII was then protected by masking the hydroxyl function with acid-catalyzed dihydropyran or ethyl vinyl ether or basic-catalyzed trialkylsilyl chloride or triphenylmethyl bromide to obtain the protected diol XIV. [See J. F. W. McOmie, "Protective Groups in Organic Chemistry", Plenum Press, New York, 1973, p. 95f].

The iodivinyl diols have utility as intermediates in producing the prostaglandin analogues of the present invention. The protected iodovinyl diol is lithiated with metallic lithium or an alkyllithium (n-butyl, sec-butyl or tert-butyl) and with the solubilized copper(I) species, for example, the hexamethylphosphorous triamide complex of copper n-propylacetylide, to produce the desired organolithiocuprate V. Specifically, (hexamethylphosphorous triamide)$_2$-copper(I)pentyne is disclosed in J. Amer. Chem. Soc., 94: 7211 (1972) and in J. Org. Chem., 31: 4071 (1966). Tri-n-butylphosphine-copper-(I)iodide is described in Inorg. Synth., 7: 9 (1963). Hexamethylphosphorous triamide-copper(I)iodide is taught in Prostaglandins, 7: 38 (1974). Preparation of phenylthio-copper is disclosed in Synthesis, 602 (1974). For a thorough review of organolithiocuprates and their utility in the synthesis of natural prostaglandins, see J. Amer. Chem. Soc., 97: 857 and 865 (1975). The organolithiocuprate V was reacted with the substituted 2-cyclopenten-1-one of formula VI as depicted in Table A.

DESCRIPTION OF THE PREFERRED EMBODIMENTS

EXAMPLE 1

1,11α,15S,19RS-tetrahydroxyprost-13E-en-9-one and 1,11α,15R,19RS-tetrahydroxyprost-13E-en-9-one
The reaction pathway is shown below.

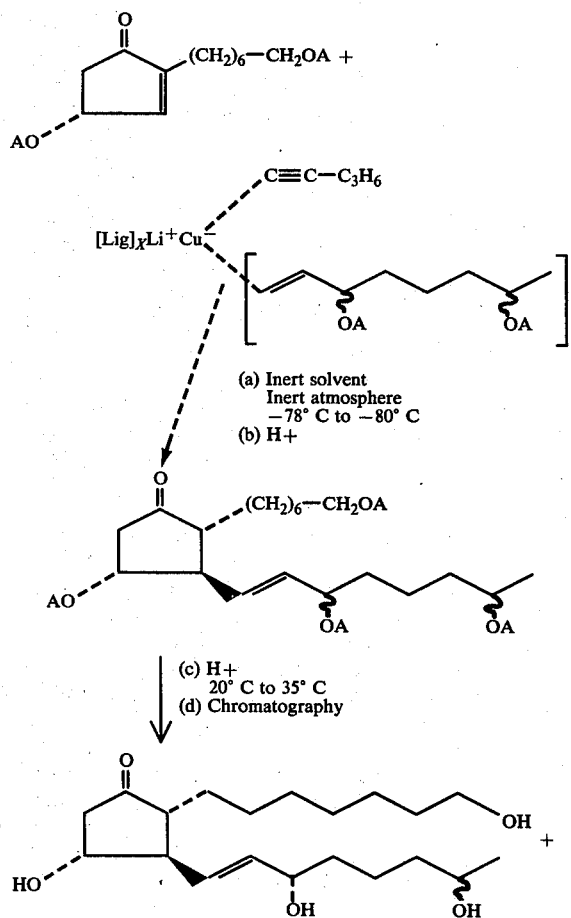

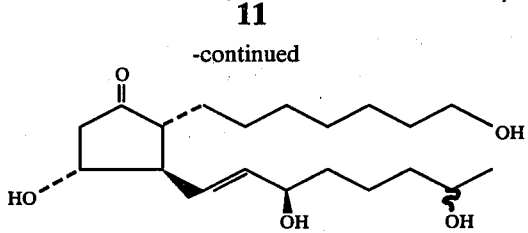

A. Preparation of Iodovinyl diol (1-Iodo-3RS,7RS-dihydroxy-1E-octene)

Preparation of 5-Ketohexanoylchloride X

A mixture of 5.50 g of 5-ketohexanoic acid commercially available from Aldrich Chemical Co., Milwaukee, Wisconsin, and 8.83 g of thionyl chloride was stirred for 16 hours at 25° C. under argon. The reaction mixture was distilled to produce 2.62 g of the hexanoylchloride as a light-yellow oil; bp 99°–104° C. (aspirator vacuum), which was contaminated with about 60% of 4-chloro-5-ketohexanoyl chloride. The material had the following spectral chracteristics: nmr δ 1.90 (s, 3, COCH$_3$), 2.0 (s, 3, CHClCOCH$_3$), 5.10 (broad t, 1, CHClCOCH$_3$); no signal for CO$_2$H observed; IR λ max 5.70, 7.50, 8.10, 8.70, 9.45μ.

Alternately, the hexanoylchloride compound can be prepared as follows from 5-ketohexanoic acid. The starting compound, 130 mg of thionyl chloride and 0.3 ml of triethylamine in 0.4 ml of methylene chloride were stirred for 1.0 hour at 25° C. The solvents were evaporated in vacuo and the residue partitioned between ether and water. The ether layer was washed with saturated aqueous sodium bicarbonate and brine, then dried over MgSO$_4$ to yield 65 mg of the hexanoylchloride as a light brown oil uncontaminated with 4-chloro-5-ketohexanoyl chloride. The pure material had the following spectral characteristics: nmr δ 1.96 (t, J=5.0Hz, 2), 2.2 (s, 3), 2.52 (m, 4).

Preparation of 1-chloro-3,7-diketo-1E-octene XI

Acetylene was passed through 69 ml of carbon tetrachloride contained in a 250 ml three-necked, round-bottomed flask equipped with a gas inlet tube, mechanical stirring, addition funnel and reflux condenser for 5 minutes. Alternately, dichloromethane can also be used as a solvent. The solvent was cooled to 0° C., 7.19 g of aluminum chloride added and acetylene passed through the slurry for an additional 5 minutes. A solution of 5.70 g of 5-ketohexanoylchloride in 6.5 ml of carbon tetrachloride was added dropwise. Acetylene was passed through the stirred mixture for an additional 4.5 hours. The reaction mixture was poured onto an ice-brine mixture, the layers separated and the aqueous layer extracted twice with ether. The combined organic layers were washed with 10% hydrochloric acid, saturated aqueous sodium bicarbonate and brine, dried over MgSO$_4$, filtered and evaporated in vacuo, to yield 2.10 g of a brown oil. This material was bulb-to-bulb distilled (vacuum pump) to yield 1.57 g of a light yellow oil. This material was combined with 1.2 g of crude product from a similar reaction sequence and purified by column chromatography (Silica Gel, 2.5% acetone in dichloromethane) to yield 585 mg of the diketooctene as a yellow oil. The material had the following spectral characteristics: nmr δ 2.15 (s, 3, COCH$_3$), 2.52 (complex, 4, CH$_2$CO), 2.00 (complex, CH$_2$CH$_2$CH$_2$), 6.50 (d, 1, =CHCl), 7.42 (d, J=14Hz, =CHCO); ir λ max 5.85, 6.30, 7.35, 10.70μ.

Preparation of 1-Iodo-3,5-diketo-1E-octene XII

A solution of 675 mg of the diketooctene in 5.8 ml of dry acetone was refluxed with 2.50 g of sodium iodide and a catalytic amount of concentrated sulfuric acid for 2 hours under argon. The acetone was evaporated in vacuo and the residue dissolved in water. The aqueous solution was extracted with ether. The extracts were washed with 10 percent aqueous sodium thiosulfate, saturated aqueous sodium bicarbonate and brine, dried over MgSO$_4$, filtered and evaporated in vacuo to yield 754 mg of the iodo-substituted diketooctene as a yellow oily solid. The material had the following spectral characteristics: nmr δ 2.15 (s, 3., COCH$_3$), 2.50 (complex, 4, CH$_2$CH$_2$CH$_2$), 7.22 (d, J=15Hz, 1, =CHI), 8.00 (d, J=15Hz, 1, =CHCO); ir λ max 5.85, 6.00, 6.40μ.

The iodo-substituted diketooctene was converted into the iodovinyl diol XIII as described below.

Preparation of 1-Iodo-3RS,7RS-dihydroxy-1E-octene XIII

A stirred solution of 495 mg of the iodo-substituted diketooctene (0° C.) in 6.0 ml of absolute methanol was treated with 619 mg of sodium borohydride (added in small portions). The reaction mixture was stirred for 1.25 hour at 0° C. under argon. The methanol was evaporated in vacuo and water added to the residue. The mixture was extracted with ether. The extracts were washed with water, saturated aqueous sodium bicarbonate and brine, dried over MgSO$_4$, filtered and evaporated in vacuo to yield 410 mg of a yellow oil. Thin layer chromatography (4:1 chloroform-acetone; Silica Gel) indicated that the reaction had not gone to completion. The crude product was resubmitted to the reaction conditions as above to yield 363 mg of crude product. The crude product was purified by column chromatography (Silica Gel, 4:1 chloroform-acetone) to afford 186 mg of the pure product as a yellow oil. The material had the following spectral characteristics: nmr δ 1.20 (d, J=6.0Hz, 1, CH$_3$), 3.10 (broad s, 2, OH), 3.6–4.3 (complex, 2, CHOH), 6.35 (d, J=14.0Hz, 1, =CHI), 6.70 (dd, J=5.0, 14.0Hz, 1, =CHCHOH); IR λ max 2.78, 2.92 (broad), 6.25μ; MS m/e 183 (p-C$_5$H$_{11}$O), 125 (p-I-H$_2$O), 107 (p-I-b 2H$_2$O); R$_f$(3:2 CHCl$_3$-acetone) 0.135.

B. Preparation of Organolithiocuprate from Iodovinyl diol (1) Preparation of 1-Iodo-3RS,7RS-bis(1-ethoxyethoxy)-1E-octene XIV The hydroxyl function of the iodovinyl diol XIII was protected as described below.

A solution of 221 mg of 1-Iodo-3RS,7RS-dihydroxy-1E-octene and 177 mg of ethyl vinyl ether in 3.0 ml of dry ether was stirred at 25° C. under argon and a few crystals of p-toluene-sulfonic acid added. The reaction mixture was stirred for 0.25 hour at 25° C., diluted with ether and washed with saturated aqueous sodium bicarbonate and brine. The organic layer was dried over MgSO$_4$, filtered and evaporated in vacuo to produce 285 mg of 1-iodo-3RS,7RS-bis(1-ethoxyethoxy)1E-octene as a yellow oil R$_f$(3:2 CHCl$_3$-acetone) 0.61. The material had the following spectral characteristics: nmr δ 1.20 (d, J=5.0Hz, 3, CH$_3$), 3.3–4.2 (complex, 6), 4.72 (broad q, 2, CHCH$_3$), 6.48 (complex, 2, =CH); IR λ max 3.32, 3.35, 3.40μ.

(2) Preparation of Organolithiocuprate from Protected Iodovinylalcohol

A solution of 291 mg of the protected iodovinylalcohol, 1-Iodo-3RS,7RS-bis(1-ethoxyethoxy)-1E-octene in 5.0 ml of dry ether was cooled to −78° C. with stirring under argon and 0.86 ml of 1.70 M t-butyllithium in pentane added dropwise. The reaction mixture was stirred for 2.3 hours at −78° C. A second solution was prepared by stirring under argon a suspension of 86 mg of copper (I) pentyne in 2.2 ml of ether, solubilized at 25° C. by the addition of 0.26 ml of hexamethylphosphorous triamide until it became homogenous. The solutions were mixed together and stirred at −78° to form the desired lithiocuprate reagent having the structural formula V.

C. The substituted 2-Cyclopenten-1-one VI 4R-(1-ethoxyethoxy)-2-[7-(1-ethoxyethoxy)heptyl]-2-cyclopenten-1-one was prepared from the appropriate 2-(ω-hydroxyalkyl)cyclopenten-1,3,4-trione as described in *Tetrahedron Letters*, 2063 (1977).

D. Prostaglandin Synthesis

The synthesis of the 1,11α,15S,19RS-tetrahydroxyprost-13E-en-9-one and 15R compound was achieved as described below.

A solution of 224 mg of the substituted cyclopentenone VI in 2.3 ml of dry ether was added dropwise to the lithiocuprate reagent V. The reaction mixture was stirred for 0.5 hour at −78° C. and 0.5 hour at −20° C. to −10° C. Dilute (2 percent) sulfuric acid was added and the reaction mixture allowed to stir an additional 10 minutes at −10° C. The mixture was filtered through a pad of Celite and the residue washed with ether. The filtrate was extracted with ether and the ether extracts washed with saturated aqueous sodium bicarbonate and brine, dried over $MgSO_4$, filtered and evaporated in vacuo to yield 252 mg of a yellow oil. The oil was stirred with 17 ml of 65-35-10 acetic acid-water-tetrahydrofuran for 2.25 hours at 25° C. The reaction mixture was evaporated in vacuo to yield 185 mg of a green oil. The oil was chromatographed (Silica Gel, 5 percent methanol in ethyl acetate) to yield 15 mg of 1,11α,15R,19RS-tetrahydroxyprost-13E-en-9-one as a yellow oil; $R_f$(2 percent methanol in ethyl acetate) 0.10; nmr δ 1.25 (d, J=6.0Hz, $CH_3$), 3.66 (broad t, 2, $CH_2OH$), 3.5–4.6 (complex, 3, CHOH), 5.72 (complex, 2, CH=CH); IR λ max 2.78, 2.95 (broad), 5.75, 5.88, 6.85, 10.40μ; MS m/e 338 (p-$H_2O$), 320 (p-$2H_2O$), 251 (p-$H_2O$-$C_5H_{11}O$), 233 (p-$2H_2O$-$C_5H_{11}O$), 223 (p-$H_2O$-$C_7H_{15}O$), 205 (p-$2H_2O$-$C_7H_{15}O$) and 37 mg of 1,11α,15S,19RS-tetrahydroxyprost-13E-en-9-one as a yellow oil; $R_f$(2 percent methanol in ethyl acetate) 0.08; nmr δ 1.15 (d, J=4.0Hz, $CH_3$), 2.2 (broad s, 4, OH), 3.68 (broad t, 2, $CH_2OH$), 3.5–4.5 (complex, 3, CHOH), 5.7 (complex 2, CH=CH); IR λ max 2.78, 2.95 (broad), 5.75, 5.88, 6.85μ; MS m/e peaks as described for the 15R,19RS compound above.

These compounds were screened to detect the effect on the guinea pig trachea in vitro.

Evaluation of the Effects on the Guniea Pig Trachea in vitro.

A male guinea pig weighing 200–500 g was killed by a blow on the head. A 20 mm length of the trachea was dissected from the animal, transferred to a petri dish containing Krebs' solution (aerated with 95% $O_2$ and 5% $CO_2$ at 37° C.), and cut longitudinally opposite the tracheal muscle. The tissue was then cut transversely three quarters of the distance across, a second cut in the opposite direction (again three quarters of the distance across the tissue) was made and the procedure was continued for the whole tissue. The ends of the trachea were pulled to form a zig-zig shaped strip. The tracheal strip used in the experiment was approximately 30 mm when extended under 0.25–0.5 g load in the tissue bath. Cotton thread was tied to one end of the tissue, and linen thread to the other. It was attached via the linen thread to a glass hook in a 5 ml isolated tissue bath containing Krebs' solution (37° C., aerated with a mixture of 95% $O_2$ and 5% $CO_2$). The opposite end was attached via cotton to an isotonic Harvard transducer (Model 386 Heart/Smooth Muscle Transducer, Harvard Apparatus). The load on the transducer lever was small, usually 0.3 g, with a range of 0.25–0.5 g, and the magnification high, 80 fold using an appropriate twin-channel pen recorder. A minimum of 30 minutes was allowed before applying a test compound to the tissue. Test compounds were then applied (in volumes of 0.5 ml) at 30 minute intervals, being in contact with the tissue for 5 minutes followed by an overflow washout time of 20 seconds.

Prostaglandin $E_1$, at a bath concentration of 0.1 mcg/ml, was then tested repeatedly on two such strips, obtained from two different animals, until two responses (the values of which are recorded) differing by no more than 25% occur. A test compound was then added to the same two strips at bath concentrations of 0.01, 0.1, 1.0, and 10.0 mcg/ml and the effects of the compound were recorded. After the test compound had been evaluated at the highest concentration, $PGE_1$ was retested at 0.1 mcg/ml (and the value of the response recorded) to insure that the viability of the strips was retained during the experiment. The mean of the effects of the test compound on the two strips was then calculated for each concentration, and it was determined whether or not the test compound produced relaxation of the tissue.

The test results for both 1,11α,15S,19RS-tetrahydroxyprost-13E-en-9-one and 1,11α,15R,19RS-tetrahydroxyprost-13E-en-9-one indicate that both compounds caused relaxation of guinea pig tracheal tissue. The prostaglandin analogues of the present invention are therefore useful as bronchodilators.

What is claimed is:

1. A compound having the formula,

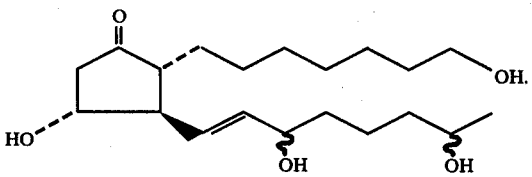

2. 1,11α,15S,19RS-tetrahydroxyprost-13E-en-9-one.

3. 1,11α,15R,19RS-tetrahydroxyprost-13E-en-9-one.

* * * * *